United States Patent
Baumoeller et al.

(10) Patent No.: US 7,452,917 B2
(45) Date of Patent: *Nov. 18, 2008

(54) EMULSIONS MADE FROM PARTICULAR EMULSIFERS

(75) Inventors: Guido Baumoeller, Leichlingen (DE); Rolf Kawa, Monheim (DE); Roland Spoerer, Kleinenbroich/Glehn (DE); Stephan Eichhorn, Gernsheim (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 101 days.

This patent is subject to a terminal disclaimer.

(21) Appl. No.: 10/466,846

(22) PCT Filed: Jan. 10, 2002

(86) PCT No.: PCT/EP02/00167

§ 371 (c)(1), (2), (4) Date: Dec. 17, 2003

(87) PCT Pub. No.: WO02/056841

PCT Pub. Date: Jul. 25, 2002

(65) Prior Publication Data

US 2004/0116542 A1 Jun. 17, 2004

(30) Foreign Application Priority Data

Jan. 19, 2001 (DE) .................. 101 02 543

(51) Int. Cl.
- *B01F 3/08* (2006.01)
- *B01F 17/34* (2006.01)
- *B01F 17/56* (2006.01)
- *A01N 25/34* (2006.01)
- *A61F 13/00* (2006.01)
- *A61K 9/70* (2006.01)

(52) U.S. Cl. ........................ 516/73; 516/74; 514/938; 424/443; 424/414

(58) Field of Classification Search ................. 516/73, 516/74; 514/938; 424/443, 414

See application file for complete search history.

(56) References Cited

U.S. PATENT DOCUMENTS

| 4,202,879 A | 5/1980 | Shelton ................. 424/66 |
| 5,069,897 A | 12/1991 | Orr ....................... 424/66 |
| 5,605,651 A | 2/1997 | Balzer .................. 424/401 |
| 5,840,943 A | 11/1998 | Ansmann et al. ......... 554/166 |
| 6,207,014 B1 | 3/2001 | de Haut et al. ........ 162/164.7 |
| 6,264,961 B1 | 7/2001 | Ansmann et al. |
| 6,576,678 B1 | 6/2003 | Bruening et al. .......... 516/22 |
| 6,596,779 B1 | 7/2003 | Jean-Noel et al. ........ 576/72 |
| 6,835,700 B1 * | 12/2004 | Nieendick et al. ........ 510/119 |
| 7,074,419 B2 | 7/2006 | Dietz et al. |
| 7,285,283 B2 * | 10/2007 | Baumoeller et al. ....... 424/400 |
| 2004/0053041 A1 * | 3/2004 | Baumoeller et al. ....... 428/326 |

FOREIGN PATENT DOCUMENTS

| DE | 20 24 051 A | 12/1971 |
| EP | 0 766 661 B1 | 4/1997 |
| EP | 1 027 921 A1 | 8/2000 |
| GB | 1 333 475 A | 10/1973 |
| JP | 11-512334 A | 10/1999 |
| JP | 1-247452 | 9/2001 |
| JP | 2006-63375 A | 3/2006 |
| WO | WO 95/16824 A1 | 6/1995 |
| WO | WO 95/35411 A1 | 12/1995 |
| WO | WO 95/35412 A1 | 12/1995 |
| WO | WO 97/30216 A1 | 8/1997 |
| WO | WO 99/67016 A1 | 12/1999 |
| WO | WO 00/68350 | * 11/2000 |

OTHER PUBLICATIONS

Balsam et al. (Eds.), Cosmetics Science and Technology, vol. 1, 2nd Edition, Chapter 11, (1972), pp. 27-104, month unknown.

Shaikh et al., "Organic Carbonates", Chem Rev., 96, (1996), pp. 951-976, month unknown, vol. 96, #3.

Leitfaden zur Inhaltsstoffdeklaration kosmetischer Mittel, Published by Industrieverband Körperpflege-und Waschmittel e.V.(IKW), Frankfurt, 3rd Edition, (1995), pp. 44-63 (Jun. 1995).

* cited by examiner

*Primary Examiner*—Daniel S Metzmaier

(57) ABSTRACT

Oil-in-water emulsions comprised of: (a) a polyol poly-12-hydroxystearate polyester; (b) an alkyl polyglycoside; (c) an oil; and (d) from 5 to 30% by weight water. When used as paper additives, the emulsions significantly improve the softness and feel of the paper products.

8 Claims, No Drawings

EMULSIONS MADE FROM PARTICULAR EMULSIFERS

BACKGROUND OF THE INVENTION

This invention relates to special, very mild emulsions which may be used as body care preparations and, in particular, for impregnating and wetting utility and hygienic paper towels.

The generic term "paper" encompasses about 3000 different types and articles which can differ, sometimes considerably, in their applications and their properties. The production of paper involves the use of numerous additives among the most important of which are fillers (for example chalk or kaolin) and binders (for example starch). For tissues and hygienic papers, which come into relatively close contact with the human skin, there is a particular need for an agreeable soft feel which is normally given to the paper by careful selection of the fibers and, in particular, by a high percentage of fresh mechanical wood pulp or cellulose. However, in the interests of economic paper manufacture and from the ecological perspective, it is desirable to use large amounts of inferior-quality wastepaper. Unfortunately, this means that the softness of the paper is significantly reduced which is troublesome to users and can even lead to irritation of the skin, particularly with frequent use.

Accordingly, there has been no shortage of attempts in the past to treat tissue papers by impregnation, coating or other surface treatments in such a way that a more agreeable soft feel is achieved. Special lotions and emulsions that are easy to apply to the paper and do not adversely affect its structure have to be developed for this purpose. To improve softness, nonionic surfactants or a combination of nonionic and anionic surfactants are often used. Polysiloxanes and cationic polymers are also used for this purpose.

International patent application WO 95/35411 relates to tissue papers coated with softening compositions which contain 20 to 80% by weight of a water-free emollient (mineral oils, fatty acid esters, fatty alcohol ethoxylates, fatty acid ethoxylates, fatty alcohols and mixtures thereof), 5 to 95% by weight of an "immobilizing" agent for the emollient (fatty alcohols, fatty acids or fatty alcohol ethoxylates containing 12 to 22 carbon atoms in the fatty group) and 1 to 50% by weight of surfactants with an HLB value of preferably 4 to 20. The Examples mentioned in this document all contain petrolatum as emollient. International patent application WO 95/35412 discloses similar tissue papers where water-free mixtures of (a) mineral oils, (b) fatty alcohols or fatty acids and (c) fatty alcohol ethoxylates are used as softeners. International patent application WO 95/16824 describes softening compositions for tissue papers containing mineral oil, fatty alcohol ethoxylates and nonionic surfactants (sorbitan esters, glucamides). In addition, International patent application WO 97/30216 (Kaysersberg) describes softening compositions for paper handkerchiefs which contain (a) 35 to 90% by weight of long-chain fatty alcohols, (b) 1 to 50% by weight of wax esters containing 24 to 48 carbon atoms, (c) 0 to 20% by weight of nonionic emulsifiers and (d) 0 to 50% by weight of mineral oil. From the performance perspective, however, the softness, processing behavior and feel of the treated papers are still in need of improvement.

Accordingly, the problem addressed by the present invention was to provide emulsions with which dry utility papers, more particularly tissue papers, and tissue cloths having a particularly agreeable soft feel could be produced. The emulsions would have excellent care properties, would resemble conventional skin-care formulations in their sensory properties and would be distinguished by particular mildness and dermatological compatibility. Another aspect of the problem addressed by the invention was to provide preparations which would even be compatible with tissue papers having a large recycled paper content. At the same time, only readily biodegradable auxiliaries would be used and the compositions would penetrate easily into the tissue, would be uniformly dispersed therein and, even in highly concentrated form, would have such a low viscosity that they would be easy to process and would allow the coated tissues to sink and dissolve in water.

DESCRIPTION OF THE INVENTION

It has now surprisingly been found that preparations based on a certain emulsifier combination and oil components with a defined water content significantly improve the softness of the paper products, have excellent sensory properties, are easy to process, even in the case of particularly critical tissue paper with a large recycled paper content, and are distinguished by particular mildness.

Accordingly, the present invention relates to o/w emulsions containing:

(a) polyol poly-12-hydroxystearates (b) alkyl polyglycosides (b) oil components and (c) 5 to 30% by weight of water.

The emulsions according to the invention have such a low viscosity, even in highly concentrated form, that they are easy to process. In a preferred embodiment, the emulsions have a viscosity at 23° C. in the range from 100 to 10,000 mPa.s, preferably in the range from 500 to 5,000 mPa.s and more particularly in the range from 2,000 to 4,000 mPa.s (Brookfield RVF, spindle 5, 10 r.p.m., 23° C.). Besides special emulsifiers and oil components, the emulsions contain 5 to 30% by weight, preferably 10 to 30 /o by weight and more particularly 15 to 30°/ by weight of water and are present as o/w emulsions. To produce the o/w emulsions, it can be of particular advantage in accordance with the invention to use water in a quantity of 20 to 30% by weight, preferably 21 to 29% by weight and more particularly 22 to 28% by weight. Papers and cloths coated/impregnated with o/w emulsion (for example toilet paper) can be wetted particularly easily by water, can sink and can therefore be more readily degraded. By virtue of their small droplet size, the emulsions penetrate very quickly into the tissues and are uniformly dispersed therein. Another advantage is that the substantially odorless preparations are ecotoxicologically safe and, in particular, are readily biodegradable. The emulsions according to the invention are also particularly suitable as very mild body care preparations (lotions).

Polyol poly-12-hydroxystearates

The polyol poly-12-hydroxystearates which form component (a) are known substances which are marketed by Cognis Deutschland GmbH, for example under the names of "Dehymuls® PGPH" and "Eumulgin® VL 75" (mixture with Coco Glucosides in a ratio by weight of 1:1) or Dehymuls® SBL. Particular reference is made in this connection to European Patent EP 0 766 661 B1. The polyol component of these emulsifiers may be derived from substances which contain at least 2, preferably 3 to 12 and more preferably 3 to 8 hydroxyl groups and 2 to 12 carbon atoms. Typical examples are (a) glycerol and polyglycerol;

(b) alkylene glycols such as, for example, ethylene glycol, diethylene glycol, propylene glycol;

(c) methylol compounds such as, in particular, trimethylol ethane, trimethylol propane, trimethylol butane, pentaerythritol and dipentaerythritol;
(d) alkyl oligoglucosides containing 1 to 22, preferably 1 to 8 and more preferably 1 to 4 carbon atoms in the alkyl group such as, for example, methyl and butyl glucoside;
(e) sugar alcohols containing 5 to 12 carbon atoms such as, for example, sorbitol or mannitol,
(f) sugars containing 5 to 12 carbon atoms such as, for example, glucose or sucrose;
(g) amino sugars such as, for example, glucamine.

Among the emulsifiers suitable for use in accordance with the invention, reaction products based on polyglycerol are particularly important by virtue of their excellent applicational properties. It has proved to be of particular advantage to use reaction products of poly-12-hydroxystearic acid with polyglycerols which have the following homolog distribution (the preferred ranges are shown in brackets):

| | |
|---|---|
| glycerol: | 5 to 35 (15 to 30) % by weight |
| diglycerols: | 15 to 40 (20 to 32) % by weight |
| triglycerols: | 10 to 35 (15 to 25) % by weight |
| tetraglycerols: | 5 to 20 (8 to 15) % by weight |
| pentaglycerols: | 2 to 10 (3 to 8) % by weight |
| oligoglycerols: | to 100% by weight |

According to the invention, it is of particular advantage to use Eumulgin® VL 74, an emulsifier mixture based on polyglycerol poly-12-hydroxystearate, lauryl glucosides and glycerol (ratio by weight 1:1:0.75) marketed by Cognis Deutschland GmbH.

The polyol poly-12-hydroxystearates are present in the emulsions according to the invention in a quantity of 2 to 20% by weight, preferably 2 to 15% by weight and more particularly 3 to 10% by weight.

Alkyl Polyglycosides

The o/w emulsions according to the invention contain alkyl polyglycosides corresponding to the general formula RO—$(Z)_x$ as another complusory component. These alkyl polyglycosides support the mildness of the compositions according to the invention, have a slight thickening effect and contribute towards improved solubilization of the fatty acid partial glycerides. In particular, they support the formation of o/w emulsions despite a very low water content (ca. 15% by weight). The alkyl polyglycosides are normally present in the emulsions according to the invention in quantities of 1 to 15% by weight, preferably in quantities of 1 to 10% by weight and more particularly in quantities of 3 to 10% by weight, based on the composition as a whole.

The are characterized by the following parameters:

The alkyl group R contains 6 to 22 carbon atoms and may be both linear and branched. Primary, linear or 2-methyl-branched aliphatic groups are preferred. Alkyl groups such as these are, for example, 1-octyl, 1-decyl, 1-lauryl, 1-myristyl, 1-cetyl and 1-stearyl. 1-octyl, 1-decyl. 1-lauryl and 1-myristyl are particularly preferred. Where so-called "oxo alcohols" are used as starting materials, compounds with an odd number of carbon atoms are dominant in the alkyl chain.

The alkyl polyglycosides usable in accordance with the invention may, for example, contain only a certain alkyl group R. However, these compounds are normally prepared from natural fats and oils or mineral oils. In this case, the alkyl groups R are mixtures corresponding to the starting compounds or to the particular method used for working up these compounds.

In particularly preferred alkyl polyglycosides, R consists essentially of $C_8$ and $C_{10}$ alkyl groups,
essentially of $C_{12}$ and $C_{14}$ alkyl groups,
essentially of $C_{16}$ and $C_{18}$ alkyl groups,
essentially of $C_8$ to $C_{16}$ alkyl groups or
essentially of $C_{12}$ to $C_{16}$ alkyl groups.

The sugar unit Z may be selected from mono- or olifosaccharides. Sugars containing 5 or 6 carbon atoms and the corresponding oligosaccharides are normally used. Examples of such sugars are glucose, fructose, galactose, arabinose, ribose, xylose, lyxose, allose, altrose, mannose, gulose, idose, talose and sucrose. Preferred sugar units are glucose, fructose, galactose, arabinose and sucrose. Glucose is particularly preferred.

The alkyl polyglycosides usable in accordance with the invention contain on average 1.1 to 5 sugar units. Alkyl polyglycosides with values for x of 1.1 to 1.7 are preferred. Alkyl polyglycosides in which x has a value of 1.2 to 1.5 and more particularly 1.4 to 1.5 are particular preferred.

A particularly preferred embodiment is characterized by the use of lauryl glucosides. These are $C_{12-16}$ fatty alcohol glucoside mixtures with an average degree of oligomerization (degree of polymerization) x of 1.4. Various fatty alcohol glucosides usable in accordance with the invention are marketed by Cognis Deutscland GmbH, for example under the name of Plantacare®.

The alkoxylated homologs of the alkyl polyglycosides mentioned may also be used in accordance with the invention. These homologs may contain on average up to 10 ethylene oxide and/or propylene oxide units per alkyl glycoside unit.

According to the invention, a particularly preferred emulsion is characterized in that the ratio by weight of polyol poly-12-hydroxystearates to alkyl polyglycosides (a:b) is 0.2-2.

Oil Components

In the context of the invention, the oil components used as component (c) of the composition according to the invention include water-insoluble organic compounds. All the oil components are preferably liquid at 20° C. In the context of the invention, insolubility in water is understood to be a solubility of less than 10% by weight at 20° C. A particularly preferred embodiment of the invention is characterized by the use of liquid, particularly thinly liquid, oil components. According to the invention, thinly liquid oil components are oil components which have a viscosity of 1 to 100 mPa.s. Thinly liquid oil components with a viscosity of 1 to 50 mPa.s and more particularly 1 to 20 mPa.s (Höppler falling ball method, Deutsche Gesellschaft für Fettchemie, DGF C-IV 7, 20° C.) are particularly preferred. The oil components are normally present in the emulsions according to the invention in a quantity of 20 to 75% by weight, based on the composition as a whole. Quantities of 30 to 70% by weight are preferred and quantities of 40 to 70% by weight particularly preferred.

Oil components usable in accordance with the invention include, for example, glycerides, hydrocarbons, silicone oils, dialkyl ethers, dialkyl carbonates, wax esters, etc. Mixtures of oil components may also be used in accordance with the invention.

Glycerides are fatty acid esters of glycerol which can be of natural (animal or vegetable) or synthetic origin. There are monoglycerides, diglycerides and triglycerides. They are known substances which may be produced by the relevant methods of preparative organic chemistry. Synthetically produced glycerides are normally mixtures of mono-, di- and triglycerides which are obtained by transesterification of the corresponding triglycerides with glycerol or by selective esterification of fatty acids. Triglycerides or glyceride mixtures with a high triglyceride content (>90% by weight) are preferred. According to the invention, fatty acids are $C_{6-24}$ fatty acids, among which $C_{6-18}$ fatty acids are suitable and $C_{8-18}$ fatty acids particularly suitable. The fatty acids may be branched or unbranched, saturated or unsaturated. According to the invention, it is preferred to use glycerides of vegetable origin which are liquid at 20° C., more particularly cocoglycerides—a mixture of mainly di- and triglycerides with $C_{8-18}$ fatty acids marketed, for example, under the name of Myritol® 331 by Cognis Deutschland GmbH.

The oil components suitable for use in accordance with the invention also include natural and synthetic, aliphatic and/or naphthenic hydrocarbons such as, for example, squalane, squalene, paraffin oils, isohexadecane, isoeicosane or polydecenes and dialkyl cyclohexanes. Hydrocarbons liquid at 20° C. are particularly suitable for ensuring good distribution of the composition on the paper.

According to the invention, other suitable oil components are silicone oils. These include, for example, dialkyl and alkylaryl siloxanes, such as for example cyclomethicone, dimethyl polysiloxane and methylphenyl polysiloxane and alkoxylated and quaternized analogs thereof. Suitable non-volatile silicone oils, such as for example polyalkyl siloxanes, polyalkylaryl siloxanes and polyether siloxane copolymers are described in Cosmetics: Science and Technology, eds.: M. Balsam and E. Sagarin, Vol.1, 1972, pp. 27-104, in U.S. Pat. No. 4,202,879 and U.S. Pat. No. 5,069,897.

Other suitable oil components are Guerbet alcohols based on fatty alcohols containing 6 to 18 and preferably 8 to 10 carbon atoms, esters of linear, saturated or unsaturated $C_{6-22}$ fatty acids with linear or branched, saturated or unsaturated $C_{6-22}$ fatty alcohols or esters of branched $C_{6-13}$ carboxylic acids with linear or branched, saturated or unsaturated $C_{6-22}$ fatty alcohols (so-called wax esters) which are preferably liquid at 20° C.

Examples of wax esters include the following typical representatives: myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Mono- or polyunsaturated wax esters, such as oleyl oleate and oleyl erucate for example, are preferably used. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols, esters of linear and/or branched fatty acids with polyhydric alcohols (for example propylene glycol, dimer diol or trimer triol) and/or Guerbet alcohols and esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms (for example Dioctyl Malate) or polyols containing 2 to 10 carbon atoms and 2 to 6 hydroxyl groups According to the invention, other suitable oil components are linear or branched, symmetrical or nonsymmetrical, saturated or unsaturated di-n-alkyl(ene)ethers containing 12 to 24 carbon atoms per alkyl(ene) group, such as for example di-n-octyl ether, di-(2-ethylhexyl)-ether, lauryl methyl ether or octyl butyl ether, didodecyl ether or dibehenyl ether, ethers liquid at 20° C. being preferred oil components.

Linear or branched, saturated or unsaturated $C_{6-22}$ fatty alcohol carbonates are also suitable. These compounds may be obtained by transesterification of dimethyl or diethyl carbonate with the corresponding hydroxy compounds by known methods. A relevant overview can be found in Chem. Rev. 96, 951 (1996). Typical examples of dialkyl(ene) carbonates are complete or partial transesterification products of dimethyl and/or diethyl carbonate with caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachidyl alcohol, gadolelyl alcohol, behenyl alcohol, erucyl alcohol and brassidyl alcohol and the technical mixtures thereof obtained, for example, in the high-pressure hydrogenation of technical methyl esters based on fats and oils. Dialkyl carbonates thinly liquid at 20° C., such as for example dihexyl, dioctyl, di-(2-ethylhexyl) or dioleyl carbonate, are particularly suitable.

In a preferred embodiment, the emulsion contains glycerides, dialkyl(ene) carbonates or a mixture of these substances as oil component. $C_{8-18}$ glycerides, di-n-octyl carbonate or a mixture thereof are particularly preferred.

Humectants/skin Moisturizers

In another preferred embodiment, the emulsion according to the invention contains at least one humectant which contributes towards improving the sensory properties and the stability of the composition and serves to regulate the skin moisture level. The humectants are normally present in a quantity of 1 to 20% by weight, preferably 5 to 15% by weight and more particularly 5 to 10% by weight.

According to the invention, suitable humectants are inter alia amino acids, pyrrolidone carboxylic acid, lactic acid and salts thereof, lactitol, urea and urea derivatives, uric acid, glucosamine, creatinine, cleavage products of collagen, chitosan or chitosan salts/derivatives and, in particular, polyols and polyol derivatives (for example glycerol, diglycerol, triglycerol, ethylene glycol, propylene glycol, butylene glycol, erythritol, 1,2,6-hexanetriol, polyethylene glycols, such as PEG-4, PEG-6, PEG-7, PEG-8, PEG-9, PEG-10, PEG-12, PEG-14, PEG-16, PEG-18, PEG-20), sugars and sugar derivatives (inter alia fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), honey and hydrogenated honey, hydrogenated starch hydrolyzates and mixtures of hydrogenated wheat protein and PEG-20-acetate copolymer. According to the invention, particularly preferred humectants are glycerol, diglycerol and triglycerol.

A particularly preferred embodiment of the composition according to the invention contains (a) 2 to 15% by weight polyglycerol poly-12-hydroxystearates; (b) 30 to 70% by weight of at least one thinly liquid oil components; (c) 1 to 15% by weight alkyl oligoglucoside; (d) 2 to 10% by weight of at least one humectant and (e) 10 to 25% by weight water.

Irritation-soothing/anti-inflammatory Agents

A preferred embodiment of the emulsion according to the invention contains at least one irritation-soothing/anti-inflammatory agent which is intended in particular to soothe inflammatory skin processes or reddened, sore skin. The irritation-soothing agent is normally present in a quantity of 0.01 to 10% by weight, preferably 0.1 to 7% by weight and more particularly 1 to 5% by weight.

According to the invention, bisabolol, allantoin and panthenol and bisabolol are particularly preferred. Vitamins and vitamin precursors and protein hydrolyzates can also promote wound healing.

Also suitable are plant extracts which often contain a synergistic combination of wound-healing/irritation-soothing substances. These extracts are normally obtained by extraction of the whole plant. In individual cases, however, it can also be preferred to prepare the extracts exclusively from flowers and/or leaves of the plant.

So far as the plant extracts suitable for use in accordance with the invention are concerned, reference is made in particular to the extracts listed in the Table beginning on page 44 of the of the 3rd Edition of the Leiffaden zur Inhaltsstoffdeklaration kosmetischer Mittel, published by the Industrieverband Körperpflege- und Waschmittel e.V. (IKW), Frankfurt.

According to the invention, the extracts of, above all, camomile, aloe vera, hamamelis, lime blossom, horse chestnut, green tea, oak bark, stinging nettle, hops, burdock root, horse willow, hawthorn, almond, pine needle, sandalwood, juniper, coconut, mango, apricot, lemon, wheat, kiwi, melon, orange, grapefruit, sage, rosemary, birch, mallow, lady's smock, creeping thyme, yarrow, thyme, balm, restharrow, coltsfoot, hibiscus, meristem, ginseng and ginger root are suitable.

Suitable extractants for the preparation of the plant extracts mentioned are water, alcohols and mixtures thereof. Among the alcohols, lower alcohols, such as ethanol and isopropanol, but especially polyhydric alcohols, such as ethylene glycol and propylene glycol, are preferably used both as sole extractant and in the form of mixtures with water. Plant extracts based on water/propylene glycol in a ratio of 1:10 to 10:1 have proved to be particularly suitable.

Consistency Factors

Consistency factors are substances which have a thickening, i.e. viscosity-increasing, effect in emulsions. The consistency factors are normally present in a quantity of 0.0 to 10% by weight, preferably in a quantity of 0.5 to 8% by weight and more particularly in a quantity of 2 to 7% by weight.

According to the invention, mono- and diglycerides or mono-diglyceride mixtures solid at 20° C., solid triglycerides and corresponding glyceride mixtures based on linear $C_{12-22}$ fatty acids and/or $C_{12-22}$ hydroxyfatty acids, fatty alcohols, waxes and soaps are particularly suitable.

According to the invention, mono-, di- or triglycerides solid at 20° C. or mixtures thereof commercially available, for example, under the names of Cutina® GMS, Syncrowax® HGLC or Novata® AB are particularly suitable as consistency factors. A glyceryl stearate marketed under the name of Cutina® MD by Cognis Deutschland GmbH is particularly preferred.

According to the invention, other suitable consistency factors are, for example, preferably saturated $C_{12-24}$ fatty alcohols which are solid at 20° C. Such alcohols include, for example, myristyl alcohol, cetyl alcohol, stearyl alcohol, erucyl alcohol, ricinoleyl alcohol, arachidyl alcohol, behenyl alcohol, brassidyl alcohol and Guerbet alcohols thereof. According to the invention, other suitable consistency factors are fatty alcohol cuts obtained by reduction of naturally occurring fats and oils such as, for example, bovine tallow, peanut oil, colza oil, cottonseed oil, soya oil, sunflower oil, palm kernel oil, linseed oil, castor oil, corn oil, rapeseed oil, sesame oil, cocoa butter and coconut oil. However, synthetic alcohols, for example the linear, even-numbered fatty alcohols from Ziegler's synthesis (Alfols®) or the partly branched alcohols from the oxosynthesis (Dobanols®) may also be used. The mixture of $C_{16}/C_{18}$ fatty alcohols marketed by Cognis Deutschland under the name of Lanette® O is particularly suitable for the purposes of the invention.

Waxes are understood to be natural or synthetic materials with the following properties: they are solid or fragile and hard in consistency, coarsely to finely crystalline, transparent or opaque, but not glass-like, and melt above 35° C. without decomposing. They are low in viscosity and non-stringing only slightly above their melting point and show highly temperature-dependent consistency and solubility. Waxes suitable for use in accordance with the present invention are, for example, natural vegetable waxes such as, for example, candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. According to the invention, it can be of advantage to use hydrogenated waxes. Natural waxes usable in accordance with the invention also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable in accordance with the invention include, for example, wax-like polyalkylene waxes and polyethylene glycol waxes, silicone waxes or esters of long-chain carboxylic acids with long-chain fatty alcohols. According to the invention, beeswax is preferably used as a consistency factor.

In the context of the invention, soaps are understood to be salts of fatty acids. Suitable consistency factors are, for example, alkali metal and alkaline earth metal and aluminium salts of $C_{12-24}$ fatty acids or $C_{12-24}$ hydroxyfatty acids, calcium, magnesium or aluminium stearate being preferred.

Co-emulsifiers

Another preferred embodiment of the emulsion according to the invention additionally contains at least one other emulsifier selected from the group of nonionic surfactants, amphoteric surfactants, zwitterionic, cationic and anionic surfactants. The composition according to the invention contains the co-emulsifiers in a quantity of normally 0 to 15% by weight, preferably 1 to 10% by weight and more particularly 3 to 10% by weight, based on the total weight of the composition.

Nonionic Emulsifiers

Nonionic emulsifiers are distinguished by their dermatological compatibility and mildness and by their favorable ecotoxicological properties. The use of a combination of nonionic emulsifiers leads to particularly fine-particle emulsions so that the stability of the composition is increased.

The group of nonionic emulsifiers includes:
(1) products of the addition of 2 to 50 mol ethylene oxide and/or 0 to 20 mol propylene oxide onto linear fatty alcohols containing 8 to 40 carbon atoms, onto fatty acids containing 12 to 40 carbon atoms and onto alkylphenols containing 8 to 15 carbon atoms in the alkyl group;
(2) $C_{12-18}$ fatty acid monoesters and diesters of addition products of 1 to 50 mol ethylene oxide onto glycerol;

(3) glycerol mono- and diesters and sorbitan mono- and diesters of saturated and unsaturated fatty acids containing 6 to 22 carbon atoms and ethylene oxide addition products thereof;

(4) alkyl mono- and oligoglycosides containing 8 to 22 carbon atoms in the alkyl group and ethoxylated analogs thereof;

(5) addition products of 7 to 60 mol ethylene oxide onto castor oil and/or hydrogenated castor oil;

(6) other polyol esters and, in particular, polyglycerol esters than polyol poly-12-hydroxystearates such as, for example, polyglycerol polyricinoleate or polyglycerol dimerate. Mixtures of compounds from several of these classes are also suitable;

(7) addition products of 2 to 60 mol ethylene oxide onto castor oil and/or hydrogenated castor oil;

(8) partial esters based on linear, branched, unsaturated or saturated $C_{6-22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) wool wax alcohols;

(10) polysiloxane/polyalkyl/polyether copolymers and corresponding derivatives;

(11) mixed esters of pentaerythritol, fatty acids, citric acid and fatty alcohol and/or mixed esters of fatty acids containing 6 to 22 carbon atoms, methyl glucose and polyols, preferably glycerol or polyglycerol, and

(12) polyalkylene glycols.

The addition products of ethylene oxide and/or propylene oxide onto fatty alcohols, fatty acids, alkylphenols, glycerol monoesters and diesters and sorbitan monoesters and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as lipid layer enhancers for cosmetic preparations from DE 20 24 051.

Since the emulsions according to the invention are o/w emulsions, it is particularly preferred to use nonionic co-emulsifiers from the group of hydrophilic o/w emulsifiers. In principle, hydrophilic co-emulsifiers are emulsifiers with an HLB value of 10 to 18 which are listed in numerous Tables and are well-known to the expert. Some of these emulsifiers are listed, for example, in Kirk-Othmer, "Encyclopedia of Chemical Technology", 3rd Edition, 1979, Vol. 8, page 913. According to the invention, the HLB value for ethoxylated products may also be calculated to the following formula: HLB=(100−L):5, where L is the percentage by weight of lipophilic groups, i.e. fatty alkyl or fatty acyl groups, in percent by weight in the ethylene oxide adducts.

Of particular advantage from the group of o/w emulsifiers are, for example, Ceteareth-12, Ceteareth-20, PEG-30 Stearate, PEG-20 Glyceryl Stearate, PEG-40 Hydrogenated Castroil Oil and Polysorbate 20.

Ampholytic surfactants are also suitable co-emulsifiers. Ampholytic surfactants are surface-active compounds which, in addition to a $C_{8/18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Zwitterionic surfactants are surface-active compounds which contain at least one quaternary ammonium group and at least one —COO$^{(-)}$ or —S)$_3^{(-)}$ group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example coco-acylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the INCI name of Cocamidopropyl Betaine is a particularly preferred zwitterionic surfactant.

Anionic surfactants are characterized by a water-solubilizing anionic group, such as for example a carboxylate, sulfate, sulfonate or phosphate group, and a lipophilic residue. Dermatologically compatible anionic surfactants are known to the expert in large numbers from relevant manuals and are commercially available. More particularly, they are alkyl sulfates in the form of their alkali metal, ammonium or alkanolammonium salts, alkyl ether sulfates, alkyl ether carboxylates, acyl isethionates, acyl sarcosinates, acyl taurines with linear $C_{12-18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as for example the dialkyl ammonium methosulfates and methyl hydroxyalkyl dialkoyloxyalkyl ammonium methosulfates marketed under the name of Stepantex® and the corresponding products of the Dehyquart® series, may be used as cationic surfactants. "Esterquats" are generally understood to be quaternized fatty acid triethanolamine ester salts. They can provide the compositions according to the invention with particular softness. They are known substances which are prepared by the relevant methods of organic chemistry. Other cationic surfactants suitable for use in accordance with the invention are the quaternized protein hydrolyzates.

Other Optional Auxiliaries and Additives

In one particular embodiment of the invention, the emulsions may contain other auxiliaries and additives, such as for example superfatting agents, thickeners, polymers, waxes, biogenic agents, deodorants, film formers, UV protection factors, antioxidants, hydrotropes, preservatives, insect repellents, self-tanning agents, solubilizers, perfume oils, dyes, germ inhibitors and the like.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable thickeners are, for example, Aerosil types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol mono-esters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L/Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®/Sandoz), copolymers of acrylic acid with dimethyl diallyl ammonium chloride (Merquat® 550/Chemviron), polyaminopolyamides, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar®C-17, Jaguar® C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, α-hydroxycarboxylic acids, amino acids, ceramides, pseudoceramides, essential oils, plant extracts and vitamin complexes.

Suitable deodorizers are, for example, antiperspirants, such as aluminium chlorhydrates, aluminium/zirconium chlorhydrates and zinc salts. These antiperspirants are used for the production of perspiration-inhibiting and deodorizing compositions and probably act by partially blocking the sweat glands through the precipitation of proteins and/or polysaccharides. Besides the chlorhydrates, aluminium hydroxylactates and acidic aluminium/zirconium salts may also be used. For example, an aluminium chlorhydrate which corresponds to the formula $[Al_2(OH)_5Cl]\cdot 2.5H_2O$ and which is particularly preferred for the purposes of the invention is commercially available under the name of Locron® from Clariant GmbH. The aluminium/zirconium tetrachlorohydrex/glycine complexes marketed, for example, by Reheis under the name of Rezal® 36G are also preferably used in accordance with the invention. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® C.A.T., Cognis Deutschland GmbH). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in the emulsions. Examples of such antibacterial agents are chitosan, phenoxyethanol and chlorhexidine gluconate. 5-Chloro-2-(2,4-dichlorophenoxy)-phenol, which is marketed under the name of Irgasan® by Ciba-Geigy of Basel, Switzerland, has also proved to be particularly effective.

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone;

propane-1,3-diones such as, for example, 1-(4-tert.butylphenyl)-3-(4'-methoxyphenyl)-propane-1,3-dione;

ketotricyclo(5.2.1.0)decane derivatives.

Suitable water-soluble substances are
2-phenylbenzimidazole-5-sulfonic acid and alkali metal, alkaline earth metal, ammonium, alkylammonium, alkanolammonium and glucammonium salts thereof;
sulfonic acid derivatives of benzophenones, preferably 2-hydroxy4-methoxybenzophenone-5-sulfonic acid and salts thereof;
sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione. The UV-A and UV-B filters may of course also be used in the form of mixtures. Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments, for example micronized zinc oxide, are preferably used in sun protection products.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, y-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to µmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (for example $ZnO$, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Some of these compounds were mentioned above among the humectants. Typical examples are
glycerol;
alkylene glycols such as, for example, ethylene glycol, diethylene glycol, propylene glycol, butylene glycol, hexylene glycol and polyethylene glycols with an average molecular weight of 100 to 1000 dalton;
technical oligoglycerol mixtures with a degree of self-condensation of 1.5 to 10 such as, for example, technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
aminosugars, for example glucamine;
dialcoholamines, such as diethaolamine or 2-aminopropane-1,3-diol.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evemyl, iraldein gamma, phenylacetic acid, geranyl acetate, benzyl acetate, rose oxide, romillat, irotyl and floramat.

Suitable dyes are any of the substances suitable and approved for cosmetic purposes. These dyes are normally used in concentrations of 0.001 to 0.1% by weight, based on the mixture as a whole.

Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenyl-biguanido)-hexane) or TCC (3,4,4'-trichlorocarbanilide). Numerous perfumes and essential oils also have antimicrobial properties. Typical examples are the active substances eugenol, menthol and thymol in nettle, mint and thyme oil. An interesting natural deodorant is the terpene alcohol farnesol (3,7,11-trimethyl-2,6,10-dodecatrien-1-ol) which is present in lime blossom oil and which smells of lily-of-the-valley. Glycerol monolaurate has also been successfully used as a bacteriostatic agent. The percentage content of the additional germ inhibitors is normally about 0.1 to 2% by weight, based on the solids component of the preparations.

The total percentage content of auxiliaries and additives may be from 1 to 50% by weight and is preferably from 5 to 40% by weight, based on the particular composition. The compositions may be produced by standard hot or cold processes and are preferably produced by the phase inversion temperature method.

FORMULATION EXAMPLES

To determine their performance properties, the stability of the emulsions according to the invention was tested and their sensory properties were evaluated in a volunteer test. Commercially available three-ply tissue papers containing 80% recycled paper and weighing 40 g/m$^2$ were treated with emulsions 1 to 6 according to the invention and with comparison preparations C1 and C2 in quantities of 2.5 g/m$^2$. Softness was then evaluated by a panel of 6 experienced examiners on a scale ranging from very soft (+++) via soft (++) to hard (++). The sensory feel on touching the tissues and on application of the emulsion to the back of the hand (very good:+++, good: ++, satisfactory: +) was also evaluated. In addition, the stability of the emulsions was evaluated after storage for 12 weeks at 23° C. (stable: +++, less stable: ++, unstable: +).

Unless otherwise indicated, the quantities in the following Examples are based on % by weight active substance of the composition as a whole. Examples 1 to 6 are formulations according to the invention, C1 and C2 are

COMPARISON EXAMPLES

| Composition/performance | 1 | 2 | 3 | 4 | 5 | 6 | C1 | C2 |
|---|---|---|---|---|---|---|---|---|
| Polyglycerol poly-12-hydroxystearate | 5.3 | 5.3 | 5.3 | 5.3 | 5.3 | 5.0 | 5.3 | — |
| Lauryl glucoside | 5.3 | 5.3 | 5.3 | 5.3 | 5.3 | 5.0 | — | 5.3 |
| Glyceryl Stearate | 3.0 | 2.0 | — | 1.5 | 3.0 | 4.0 | 2.0 | 3.0 |
| Polysorbate 20 | — | — | — | — | — | — | 1.0 | 3.0 |
| Dicocoylethyl Hydroxyethylmonium Methosulfate | — | — | — | — | — | 1.12 | — | — |
| Propylene Glycol | — | — | — | — | — | 0.38 | — | — |
| C$_{16-18}$ alkyl polyglucoside | — | 1.5 | — | — | 1.0 | — | — | — |
| C$_{16-18}$ fatty alcohol | — | 1.5 | — | — | 1.0 | — | — | — |
| Cocoglyceride | 30.0 | 25.0 | 30.0 | 30.0 | 30.0 | 30.0 | — | 30.0 |
| Di-n-octyl carbonate | 30.0 | 30.0 | 20.0 | 30.0 | — | 25.0 | — | 25.0 |
| Oleyl Erucate | — | — | 5.0 | — | — | — | 25.0 | 0 |
| Decyl Oleate | — | — | — | — | 30.0 | — | 25.0 | — |
| Citric acid | 0.1 | 0.1 | — | 0.1 | 0.1 | 0.1 | 0.1 | — |
| Bisabolol | 1.5 | 2.0 | 1.5 | 1.5 | 1.5 | 1.5 | 1.5 | 1.5 |
| Glycerol | 4.0 | 5.0 | 4.0 | 4.0 | 4.0 | 5.0 | 5.0 | 5.0 |
| Perfume | 0.35 | 0.5 | 0.35 | 0.35 | 0.35 | 0.5 | 0.35 | 0.35 |
| Phenonip ® | 1.0 | 1.0 | 1.0 | 1.0 | 1.0 | 1.0 | 1.0 | 1.0 |
| Water | to 100 | | | | | | | |
| Softness | +++ | +++ | +++ | +++ | +++ | +++ | + | + |
| Stability | +++ | +++ | ++ | ++ | +++ | ++ | + | + |
| Sensory evaluation | +++ | +++ | +++ | +++ | ++ | +++ | + | + |

The invention claimed is:

1. An oil-in-water emulsion comprising: (a) from 2-20% by weight of a polyol poly-12-hydroxystearate; (b) from 1-15% by weight of an alkyl polyglycoside; (c) from 20-75% by weight of an oil which is liquid at 20° C.; and (d) from 5 to not more than 30% by weight water, wherein the viscosity of the emulsion is from 100 to 10,000 mPa.s at 23° C.

2. The emulsion of claim 1 wherein the ratio by weight of polyol poly-12-hydroxystearate to the alkyl polyglycoside is from 0.2 to 2.0.

3. The emulsion of claim 1 wherein the oil is selected from the group of glycerides, dialkyl(ene) carbonates and mixtures thereof.

4. The emulsion of claim 1 further comprising a humectant.

5. The emulsion of claim 1 further comprising an irritation-soothing agent.

6. The emulsion of claim 1 further comprising a thickener.

7. The emulsion of claim 1 further comprising an emulsifier selected from the group of a nonionic surfactant, an amphoteric surfactant, a zwitterionic surfactant, a cationic and an anionic surfactant.

8. An oil-in-water emulsion comprising: (a) from 2 to 15% by weight of polyglycerol poly-12-hydroxystearate; (b) from 30 to 70% by weight of at least one thinly liquid oil component which is liquid at 20° C.; (c) from 1 to 15% by weight alkyl oligoglucoside; (d) from 2 to 10% by weight of at least one humectant and (e) from 10 to not more than 25% by weight of water, wherein the viscosity of the emulsion is from 100 to 10,000 mPa·s at 23° C.

* * * * *